United States Patent [19]

Gane et al.

[11] Patent Number: 4,520,118

[45] Date of Patent: May 28, 1985

[54] CATALYTIC ACTIVITY OF ALUMINOSILICATE ZEOLITES

[75] Inventors: Brian R. Gane, Ottershaw; Philip Howard, Teddington, both of England

[73] Assignee: The British Petroleum Company p.l.c., London, England

[21] Appl. No.: 580,673

[22] Filed: Feb. 16, 1984

[30] Foreign Application Priority Data

Mar. 9, 1983 [GB] United Kingdom ................ 8306531

[51] Int. Cl.[3] .......................... B01J 25/04; B01J 29/06
[52] U.S. Cl. ...................................... 502/53; 502/55; 502/61; 502/85
[58] Field of Search ...................... 502/61, 85, 64, 73, 502/55, 53

[56] References Cited

U.S. PATENT DOCUMENTS 3,428,550  2/1969  Erickson et al. ............... 502/64 X
3,706,694  12/1972  Young ............................ 502/73 X

FOREIGN PATENT DOCUMENTS 5909  12/1979  European Pat. Off. ............ 502/64

*Primary Examiner*—Carl F. Dees
*Attorney, Agent, or Firm*—Brooks Haidt Haffner and Delahunty

[57] ABSTRACT

This invention relates to a method of improving the catalytic activity of a freshly made zeolite loaded with gallium ions by first treating with steam and then with hydrogen. Steam and hydrogen treatment may be carried out before or after loading with gallium simultaneously or successively. It has been found that a combination of steam and hydrogen treatments gives high conversions of hydrocarbon feeds and high selectivity to aromatics.

17 Claims, No Drawings

CATALYTIC ACTIVITY OF ALUMINOSILICATE ZEOLITES

The present invention relates to a method of improving the catalytic activity of aluminosilicate zeolites, and in particular the activity of freshly made zeolites loaded with a gallium compound or gallium ions.

Aluminosilicate zeolites and their gallium loaded derivatives are well known for their ability to catalyse hydrocarbon conversion reactions. These zeolites and their methods of preparation are claimed and described in our British patent specification Ser. No. 1561690 and in our published copending European patent application Nos. 002900 and 0024930. Such zeolites are generally prepared by reacting in aqueous solution a mixture of a source of silica, a source of alumina, a source of alkali metal and a nitrogen containing base in appropriate proportions. The zeolite is then allowed to crystallise from the solutions by maintaining the solution at an appropriate elevated temperature under autogenous pressure. For most uses, it is necessary to remove the nitrogen containing base and the alkali metal from the "as synthesised" zeolite. (By "as synthesised" is meant here and throughout the specification a zeolite which is separated from its mother liquor and washed with neutral, acidic or alkaline aqueous solutions). Various methods have hitherto been used to achieve this eg calcination in air followed by ion-exchange with hydrogen or ammonium cations. It is also known that the zeolite can be bound before or after calcination or ion exchange or both with a suitable matrix material such as silica or alumina to improve its mechanical stability. It is also known to load the zeolite, before or after binding, with catalytically active ions or compounds such as those derived from gallium or aluminium by for example ion-exchange or impregnation techniques.

The yield of aromatics from $C_2$ and higher hydrocarbons using these catalysts is high but contains a small but significant amount of higher boiling polynuclear aromatics such as naphthalene and methylnaphthalenes. These polynuclear aromatics are not only undesirable in gasoline blending components but also give rise to coking problems on the catalyst thus reducing its cycle life.

Prior art publications refer to various methods of activating these zeolites whether or not loaded with an additional catalytic component. These include treatment of the zeolite with hydrogen, oxygen or a combination of the two in sequence. However, if the calcination stage during the preparation of the zeolite is carried out at or about 550° C. under substantially dry conditions, the resulting catalysts have a high initial activity in hydrocarbon conversion reactions but also produce coke at a high rate and therefore deactivate rapidly.

It is also generally known that treating the catalysts with steam alone at elevated temperature significantly reduces the activity of the catalyst due to dealumination. U.S. Pat. No. 3,855,115 suggests the addition of rhenium to the catalyst to reduce polynuclear aromatics but this expedient also reduces the overall selectivity to aromatics.

It has now been found that by subjecting a gallium loaded zeolite during its preparation to a combination of steam and hydrogen treatments, the activity and cycle life of the catalyst can be significantly improved and the formation of polynuclear aromatics reduced during conversion of open chain hydrocarbons to aromatics.

Accordingly, the present invention is a process for activating an aluminosilicate zeolite loaded with a gallium compound as catalyst said process comprising bringing into contact the zeolite, before or after loading thereof with gallium, with steam and concurrently or separately with hydrogen, both stages being carried out at an elevated temperature.

The expression "activating an aluminosilicate zeolite" as used herein and throughout the specification means activating unused, freshly prepared zeolites and restoring the activity of zeolites which are partially or wholly deactivated during hydrocarbon conversion.

The zeolites which may be activated by the process of the present invention are aluminosilicates which preferably have a high silica to alumina ratio, ie greater than 5:1. Methods of preparing such zeolites are described for instance in our published European patent application Nos. 0024930 and 0030811. Particularly useful zeolites are MFI-type zeolites.

Zeolites are best characterised according to framework structure type, i.e. on the topology of the framework, irrespective of composition, distribution of different tetrahedral atoms, cell dimensions and symmetry. A code consisting of three capital letters has been adopted for each known structure type following the recommendations by IUPAC on zeolite nomenclature ("Chemical Nomenclature, and Formulation of Compositions, of Synthetic and Natural Zeolites," IUPAC yellow booklet, 1978) and a compilation of 38 known zeolite structure types has been published by The Structure Commission of the International Zeolite Association ("Atlas of Zeolite Structure Types", by Meier, W. M. and Olsen, D. H. (1978), distributed by Polycrystal Book Service, Pittsburgh, Pa, USA).

The activation process of the present invention is particularly effective on zeolites which are low in their content of sodium or other alkali metal ions.

The steam treatment may be carried out on the zeolite whether or not it has been located with a catalytically active component such as eg gallium oxide. Moreover, the steam treatment may be carried out as part of a regeneration procedure on a catalyst which has been partially or wholly deactivated in use.

The various embodiments of the present invention showing the sequence in which the steps of calcination (C), steaming (S), loading (G) with an active catalyst component, and binding (B) may be carried out on the zeolite can be notationally summarised as follows:

1. C (s)* G B
2. C (s)* B G
3. C S G B
4. C S B G
5. C G S B
6. C G B S
7. C B G S
8. C B S G
9. B C (s)* G
10. B C S G
11. B C G S

*C (s)-represents simultaneous calcination and steaming. Of these, sequences 1, 3, 6, 9, 10 and 11 are particularly preferred.

The steam treatment of the zeolite in any of the above embodiments is suitably carried out using steam as such or a carrier gas stream comprising steam. The carrier gas stream may be a gas inert under the reaction conditions e.g. nitrogen or air. The gas stream used for steam treatment suitably contains between 1 and 100% volume of steam, preferably between 10 and 100% v/v steam.

The steam treatment is suitably carried out at a pressure of between 0.01 and 1.0 MPa, preferably at 0.1 MPa and a temperature between 300° and 750° C., preferably between 500° and 700° C. for a duration of between 5 minutes and 200 hours, preferably between 1 and 12 hours. Increasing the severity of one or more parameters may allow reduction of the severity of other relevant parameters. For instance, raising the steaming temperature can be expected to shorten the duration of steaming needed.

The steam treatment referred to herein may be preceded by, concurrent with or followed by the hydrogen treatment. The hydrogen treatment step is preferably carried out after the zeolite has been loaded with the gallium compound. That is, the gallium loaded zeolite may for instance be treated with air and/or hydrogen in either order at an elevated temperature prior to, during or after the steam treatment step. However, the steam treatment step may precede the gallium loading step in which case it is preferred that the hydrogen treatment follows steam treatment and gallium loading.

The hydrogen treatment is suitably carried out in a gaseous stream containing between 1 and 100% volume of hydrogen, preferably between 30 and 100% v/v hydrogen. The hydrogen treatment may be carried out at 450° to 700° C., preferably 525°–650° C. for 5 minutes to 200 hours, preferably for 1 to 20 hours and a pressure of 0.01 to 1.0 MPa, preferably at 0.1 MPa. Increasing the severity of one or more parameters may allow reduction of the severity of one of the other parameters. For instance, raising the temperature of hydrogen treatment may reduce the duration of this treatment needed.

The steam and hydrogen treated gallium-loaded zeolite catalyst may, if desired, have a final treatment in an oxidising atmosphere such as eg air, at elevated temperature.

The steam and hydrogen treatments may be carried out on a gallium loaded zeolite, which has been wholly or partially deactivated in use as a hydrocarbon conversion catalyst, as part of a regeneration procedure to restore and improve the activity thereof.

The steam of hydrogen treatment of the zeolite may be preceded or followed by one or more conventional oxidation, calcination or reduction steps.

The present invention is further illustrated with reference to the following Examples.

EXAMPLES 1–3

1(a) Catalyst Preparation

An MFI zeolite (SiO$_2$:Al$_2$O$_3$ molar ratio 34.9) prepared from a gel containing diethanolamine as described in Example 1(a) of EPA 0024930 was used.

Nitric acid (180 ml of 70%) was added to a suspension of zeolite (250 g) in water (1070 ml) and the mixture stirred for 30 minutes. The zeolite was filtered off and washed with 4×500 ml aliquots of water. After removal of the bulk of the water by filtration, the washed zeolite was dried at 100° C. under vacuum for 16 hours. The dried zeolite was heated in a muffle furnace to 550° C. in a stream of air, and this temperature was maintained for 60 hours. The calcined zeolite (175 g) was refluxed with a dilute solution of gallium nitrate (4.4 g of Ga) for 4 hours, filtered, washed with 4×500 ml of water and dried. A portion of the dried powder (157 g) was mixed with Ludox AS 40 (Registered Trade Mark, 127 g) and water, dried in a vacuum oven and crushed to 12/30 mesh.

(b) Treated Catalysts for Small-Scale Experiments

A portion of the silica bound catalyst produced in Section (a) above and contained in a quartz tubular reactor was heated to 550° C. in flowing nitrogen. A mixture of steam (18.3% vol) in nitrogen was then passed over the catalyst for 2 hours. A portion of this catalyst was heated in flowing nitrogen to 650° C. Hydrogen was then passed over the catalyst for 4 hours before the catalyst was cooled to room temperature under nitrogen.

2. Small-Scale Testing of Catalysts

The catalyst (5.66 g) treated with steam and hydrogen as in Section 1(b) above was loaded into a quartz reactor which was placed in a furnace that was heated to 500° C. Air was passed over the catalyst for 4 hours, the equipment flushed with nitrogen, and butane passed over the catalyst at such a rate as to give a contact time, calculated at 550° C./atmospheric pressure, of 1.6 to 1.7 seconds.

The performance of the catalysts are assessed by comparing the conversions and selectivities obtained. These are defined as follows:

% C$_3$ to C$_4$ Conversion = (100 − %wt of total C$_3$ and C$_4$ compounds in the reaction products)

(The inclusion of C$_3$ in this conversion is necessary as it has been found that propane is readily produced from butane, but also reacts to produce liquid products at a rate dependent upon the catalyst activity).

$$\text{Selectivity (wt \%)} = \frac{\text{\% wt Yield of Products Containing Five or More Carbon Atoms}}{\text{\% C}_3 + \text{C}_4 \text{ Conversion}} \times 100$$

The increases in the conversion and selectivity obtained by the hydrogen treatment of a steamed catalyst are clearly shown in Table 1 in which the results obtained over three catalysts during the period 0.5 to 1.5 hours on stream are compared. Each run was continued for 6 hours, after which the catalyst was cooled to room temperature in flowing nitrogen. The quantity of carbon on the catalyst was then determined by microanalysis. The considerable decrease in carbon formation brought about by steaming and the slight increase caused by hydrogen treatment are also shown in Table 1. The catalyst cycle-life that would be expected in longer runs over these catalysts is inversely related to the rate of carbon formation.

TABLE 1

REACTION OF n-BUTANE OVER Ga/ZEOLITE
Atmospheric Pressure

| | C$_3$ + C$_4$ Conversion | Selectivity | Carbon (% wt on Catalyst) |
|---|---|---|---|
| Catalyst as prepared | 73.8 | 61.5 | 2.2 |
| Steam treated | 67.8 | 64.8 | 1.1 |
| Steam and hydrogen treated | 77.3 | 67.1 | 1.3 |

TABLE 2

REACTION OF n-BUTANE OVER Ga/ZEOLITE
535° C./6 bar abs/2 LHSV

| | Time on stream (h) | | | | | |
|---|---|---|---|---|---|---|
| | 3 | | 24 | | 60 | |
| | $C_3 + C_4$ Conversion | Selectivity | $C_3$ to $C_4$ Conversion | Selectivity | $C_3$ to $C_4$ Conversion | Selectivity |
| Catalyst as prepared | 90.8 | 47.7 | 58.5 | 59.1 | — | — |
| Steam treated | 85.0 | 53.6 | 81.1 | 54.4 | 75.1 | 55.9 |
| Steam and hydrogen treated | 89.7 | 52.8 | 86.1 | 54.5 | 80.6 | 57.8 |

3. Large-Scale Testing of Catalysts

The catalyst, prepared as described in Section 1(a), contained in a stainless steel reactor was heated to 550° C. in a stream of nitrogen. Air was passed over the catalyst for 2 hours before the reactor was purged with nitrogen and the pressure increased to 6 bar absolute. Butane was then fed over the catalyst with a LHSV of 2 and the reactor heaters adjusted to give an average bed temperature of 535° C. Samples of liquid and gaseous products were measured and analysed at selected two hour periods throughout the experiment which was terminated after 51 hours. The catalyst was then regenerated by burning off the deposited carbon in a dilute air stream. Following the regeneration the catalyst was heated at 550° C. for 2 hours in a stream of steam (19.6% vol) in nitrogen before use in a further experiment under the same conditions as described previously. As the decline in activity was slower over the steamed catalyst, the experiment was continued 121 hours before the catalyst was again regenerated. The carbon free catalyst was heated in nitrogen to 650° C. and hydrogen was then passed over the catalyst for 4 hours. The hydrogen treated catalysts were tested under the same conditions as described above, including, in this case, the air treatment before the run.

The conversions and selectivities measured during some of the test periods of the three experiments are shown in Table 2. A comparison of the conversions obtained at equivalent times shows the increased activity of the final catalyst, and a comparison of the selectivities obtained at near equivalent conversions shows the improvement effected by the hydrogen treatment. The continuing increase in activity observed after 60 hours on stream in the final experiment showed that any deleterious effect of hydrogen treatment on catalyst cycle-life, as might be expected from the slight increase in carbon deposition observed in the small-scale tests, was small.

EXAMPLES 4–6 AND COMPARATIVE TESTS 1–6

(A) Preparation of Bound Zeolite

A liquor-free MFI-type zeolite ($SiO_2:Al_2O_3$ molar ratio=37.3) was prepared in a manner substantially similar to that described in Example 1(a) of our European patent application No. 0024930. (The starting gel had a relative molar composition $2.2Na_2O:18.3DEA:Al_2O_3:36.3SiO_2:532H_2O$). It was washed with dilute nitric acid (ca 13 wt % $HNO_3$, ca 5 ml solution:1 g zeolite) then dried and bound with alumina and calcined at 550° C. for three hours in dry flowing air.

(B) EXAMPLE 4 (Gallium loading followed by steam treatment and then hydrogen treatment)

(i) A sample of the bound zeolite from (A) above was brought into contact first with slightly acidic water (pH 5 to 6) (ratio 4:5 ml water:1 g solid zeolite) and then with an aqueous solution of gallium nitrate (0.36M titrated to pH 2.7 with aqueous ammonia) in the ratio of 1 ml solution:1 g of solid zeolite. The resultant mixture was then rapidly heated to reflux and maintained at the refluxing temperature for 4 hours. The resultant product was filtered while hot, the solid gallium loaded product washed thoroughly with water and then dried at 110° C. for 16 hours to give the gallium loaded zeolite catalyst (gallium loading was 0.73% w/w).

(ii) A sample of the gallium loaded zeolite from (i) above was heated in a tube furnace to 550° C. in flowing air. Steam (20% v/v in air) was then passed over the zeolite for 2 hours and thereafter the zeolite was allowed to cool in air.

(iii) 6 ml of the resultant gallium-loaded, steamed, bound zeolite catalyst from (ii) above was activated by placing in a tubular reactor, heated to 550° C. and maintained at that temperature for 4 hours in dry flowing air. The heated catalyst was then flushed with flowing nitrogen.

(iv) The average bed temperature of the catalyst was maintained at 535° C. by external heating and brought into contact with n-butane (1 bar absolute presure and 5 WHSV) for 5 hours.

(v) The catalyst which had by now been partially deactivated was then flushed with nitrogen and cooled, and then regenerated by calcining in flowing air, gradually raising the temperature to 550° C.

(vi) The calcined catalyst from (v) above was again flushed with nitrogen while heating to 600° C., then maintained in flowing hydrogen at 600° C. for 16 hours. The hydrogen treated catalyst was again flushed with nitrogen while cooling to 550° C. with nitrogen and then contacted with flowing air at 550° C. for 30 minutes and then reflushed with nitrogen.

(vii) The activity of the catalyst so regenerated was retested as in (iv) above. The results of this final test are shown in Table 3 below.

EXAMPLE 5 (Gallium loading followed by hydrogen treatment then steam treatment)

(i) A sample of the gallium loaded, bound zeolite from Example 4(i) above was loaded into a reactor and was successively heated first in hydrogen and then in air as in Example 4(vi) above. The catalyst so produced was tested for its ability to convert n-butane under the same conditions as described 4(iv) above.

(ii) The resultant partially deactivated catalyst was regenerated in the same manner as described in Example 4(v) above, removed from the reactor and steam treated as described in Example 4(ii). The steam treated catalyst was returned to the reactor and activated and tested for its ability to convert n-butane under the same conditions as described in Examples 4(iii) and 4(iv)

respectively. The results of this final test are shown in Table 3 below.

EXAMPLE 6 (Steam treatment, then gallium loading and then hydrogen treatment)

(i) A sample of the bound zeolite from Section (A) above was steam treated and then loaded with gallium under the same conditions as described in Example 4(ii) and then 4(i) respectively.

(ii) A sample of this steam-treated, gallium loaded zeolite was activated and then tested for its ability to convert n-butane under the same conditions as described in Example 4(iii) and then 4(iv) respectively.

(iii) The resultant partially deactivated catalyst was regenerated as in Example 4(v) above. The regenerated catalyst was heated first in hydrogen and then air as in Example 4(v) above. The catalyst so produced was retested for its ability to convert n-butane under the same conditions as described in Example 4(iv) above. The results of this final test are shown in Table 3.

COMPARATIVE TEST 1 (Gallium loading, then only steam treatment—no hydrogen treatment)

This is illustrated by the gallium loaded, bound zeolite prepared and tested for n-butane conversion above in Example 4(i) to 4(iv) inclusive. The results are shown in Table 3.

COMPARATIVE TEST 2 (Gallium loading then only hydrogen treatment—no steam treatment)

This is illustrated by the hydrogen treated gallium-loaded, bound zeolite prepared and tested for n-butane conversion in Example 5(i) above. The results are shown in Table 3 below.

COMPARATIVE TEST 3 (Only steam treatment then gallium loading—no hydrogen treatment)

This is illustrated by the steam treated, bound zeolite, subsequently loaded with gallium, prepared and tested for n-butane conversion in Example 6(i) then 6(ii) above. The results are shown in Table 3 below.

COMPARATIVE TEST 4 (Gallium loading only—no steam or hydrogen treatments)

A sample of the gallium loaded, bound zeolite prepared as in Example 4(i) above was then activated as in Example 4(iii) above. The resultant catalyst was then tested for its ability to convert n-butane under the same conditions as in Example 4(iv) above. The results are shown in Table 3 below.

COMPARATIVE TEST 5 (No gallium loading or steam or hydrogen treatments)

A sample of the bound zeolite from Section (A) was activated as in Example 4(iii) then tested for butane conversion as in Example 4(iv). The results of this test are shown in Table 3 below.

COMPARATIVE TEST 6 (Only hydrogen and steam treatments—no gallium loading)

A sample of the bound zeolite from Section (A) was steamed as in Example 4(ii) then contacted with aqueous ammonium nitrate solution (0.8M, 12.5 ml/g steamed bound zeolite). The resultant mixture was then rapidly heated to reflux and maintained at the refluxing temperature for four hours. The resultant solid was filtered while hot. The solid product was washed thoroughly with water then dried at 110° C. for 16 hours. [The purpose of the ammonium exchange step is to simulate the exchange procedure use to gallium load in the Examples (but not to gallium load in this case) in order to give a realistic comparison]. The resultant solid was activated as in Example 4(iii) then tested for n-butane conversion as in Example 4(iv). The resultant partially deactivated catalyst was regenerated and hydrogen-tested as in Example 4(v) and Example 4(vi) then retested for n-butane conversion as in Example 4(iv). The results of this final test are shown in Table 3 below.

The above results (Examples 4–6, Tests 1–6) clearly show that:
(a) a combination of steam and hydrogen treatments at elevated temperatures gives high feed conversions and selectivities to aromatics but low selectivities to di- and polynuclear aromatics,
(b) The relative position of the steaming step during catalyst preparation is unimportant, and
(c) no single treatment with hydrogen alone or steam alone gives the desired results, ie high feed conversion and selectivity to aromatics with low selectivities to di- and polycyclic aromatics.
(d) The effect is especially beneficial for systems which include a Ga-loading step.

TABLE 3

| | Catalytic Performance 0.5–1 HOS | | | | | | | | |
|---|---|---|---|---|---|---|---|---|---|
| | Example 4 | Example 5 | Example 6 | Test 1 | Test 2 | Test 3 | Test 4 | Test 5 | Test 6 |
| $C_3 + C_4$ Conversion (wt %) (1) | 63.6 | 63.8 | 65.4 | 53.6 | 73.8 | 71.2 | 67.2 | 44.8 | 43.5 |
| Aromatics Selectivity** (wt %) (2) | 63.7 | 63.8 | 63.2 | 54.6 | 63.5 | 63.8 | 59.5 | 40.8 | 41.3 |
| PCA*/ARO** (wt %) (3) | 3.2 | 2.7 | 3.9 | 3.2 | 6.0 | 5.1 | 5.8 | 3.6 | 1.9 |

*Polycyclic Aromatics
**Total Aromatics
(1) $100 - (\text{Yield } C_3 + C_4)$ wt %
(2) $\frac{100 \times (\text{Yield Aromatics})}{C_3 + C_4 \text{ Conversion}}$ wt %
(3) $\frac{100 \times (\text{Yield PCA})}{(\text{Yield Aromatics})}$ wt %

We claim:
1. A process for activating an aluminosilicate zeolite loaded with a gallium compound as catalyst said process comprising bringing into contact the zeolite, before or after loading thereof with gallium, with steam and concurrently or separately with hydrogen, both stages being carried out at an elevated temperature.

2. A process according to claim 1 wherein the zeolites are aluminosilicates which have a silica to alumina ratio greater than 5:1.

3. A process according to claims 1 or 2 wherein the zeolite is subjected to a sequence of treatments comprising calcination (C), steaming (S), loading with a gallium compound (G), and binding (B) said sequence being selected from:
- (a) C (s)* G B
- (b) C (s)* B G
- (c) C S G B
- (d) C S B G
- (e) C G S B
- (f) C G B S
- (g) C B G S
- (h) C B S G
- (i) B C (s)* G
- (j) B C S G
- (k) B C G S wherein *C (s)-represents simultaneous calcination and steaming.

4. A process according to claim 1 or 2 wherein the steam treatment of the zeolite is suitably carried out using steam as such or a carrier gas stream comprising steam.

5. A process according to claim 1 or 2 wherein the steam treatment is carried out at a pressure of between 0.01 and 1.0 MPa and a temperature between 300° and 750° C., duration of between 5 minutes and 200 hours, preferably between 1 and 12 hours.

6. A process according to any one of the preceeding claims wherein the hydrogen treatment step is carried out after the zeolite has been loaded with the gallium compound.

7. A process according to claim 1 or 2 wherein the steam treatment step precedes the gallium loading step and the hydrogen treatment follows steam treatment and gallium loading.

8. A process according to claim 1 or 2 wherein the hydrogen treatment is carried out in a gaseous stream containing between 1 and 100% volume of hydrogen.

9. A process according to claim 1 or 2 wherein the hydrogen treatment is carried out at 450° to 700° C. and a pressure of 0.01 to 1.0 MPa.

10. A process according to claim 1 wherein the steam and hydrogen treatments are carried out on a gallium loaded zeolite, which has been wholly or partially deactivated in use as a hydrocarbon conversion catalyst, as part of a regeneration procedure to restore and improve the activity thereof.

11. A process according to claim 3, wherein said sequence of treatments is selected from:
- (a) C (s)* G B
- (c) C S G B
- (f) C G B S
- (i) B C (s)* G
- (j) B C S G
- (k) B C G S wherein *C (s)-represents simultaneous calcination and steaming.

12. A process according to claim 3, wherein said sequence of treatments is C (s)* G B.

13. A process according to claim 3, wherein said sequence of treatments is C S G B.

14. A process according to claim 3, wherein said sequence of treatment is C G B S.

15. A process according to claim 3, wherein said sequence of treatments is B C (s)* G.

16. A process according to claim 3, wherein said sequence of treatment is B C S G.

17. A process according to claim 3, wherein said sequence of treatments is B C G S.

* * * * *

UNITED STATES PATENT AND TRADEMARK OFFICE
CERTIFICATE OF CORRECTION

PATENT NO. : 4,520,118
DATED : May 28, 1985
INVENTOR(S) : BRIAN R. GANE and PHILIP HOWARD It is certified that error appears in the above-identified patent and that said Letters Patent is hereby corrected as shown below:

Col. 3, line 45, "steam of hydrogen" should read --steam or hydrogen--

Signed and Sealed this

Seventeenth Day of September 1985

[SEAL]

Attest:

DONALD J. QUIGG

Attesting Officer

Commissioner of Patents and
Trademarks—Designate